United States Patent [19]

Bailey

[11] 4,043,193
[45] Aug. 23, 1977

[54] METHOD AND APPARATUS FOR MEASURING VOLUME AND DENSITY OF FLUIDS IN A DRILLING FLUID SYSTEM

[75] Inventor: John M. Bailey, Houston, Tex.

[73] Assignee: Bailey Mud Monitors Inc., Thibodaux, La.

[21] Appl. No.: 711,297

[22] Filed: Aug. 3, 1976

[51] Int. Cl.$^2$ ............................................. E21B 47/04
[52] U.S. Cl. ...................................... 73/155; 73/302; 73/438
[58] Field of Search ................. 73/155, 438, 299, 302, 73/301

[56] References Cited

U.S. PATENT DOCUMENTS

| | | | |
|---|---|---|---|
| 2,722,123 | 11/1955 | Kangas | 73/438 R |
| 3,407,661 | 10/1968 | Kanauth | 73/155 UX |

Primary Examiner—Jerry W. Myracle
Attorney, Agent, or Firm—Wilkinson, Mawhinney & Theibault

[57] ABSTRACT

This invention provides an apparatus and method which will furnish to an operator drilling an oil well, critical information relative to drilling fluid conditions in portions of and/or in the total fluid circulation system; such information as fluid densities, both in-flow and out-flow, volume in each fluid pit and/or total volume in the entire system, together with a continuous indication of whether there have been gains or losses of drilling fluids. This invention obtains this information more accurately than present methods known to the art, and further with the added feature that no moving part or parts need come into physical contact with the drilling fluids.

8 Claims, 3 Drawing Figures

METHOD AND APPARATUS FOR MEASURING VOLUME AND DENSITY OF FLUIDS IN A DRILLING FLUID SYSTEM

BACKGROUND OF THE INVENTION

Since it is well established that blowouts, subsurface structure damage, costly breakdowns with stuck pipe, and several other undesirable side-effects are directly associated with the drilling fluid (mud) circulation system in drilling a well, a method and apparatus for providing essential and accurate fluid systems data will be of great use and service to the industry and the art. By the very nature of drilling fluids, (drilling mud) as is well known by those familiar with the art, densities are continually changing, foreign materials and particles are constantly introduced into the system, and those fluid measuring devices presently in use have moving parts which are designed to come into actual physical contact with the drilling fluids during their operation. For example, fluid pit floats, which measure pit levels must float on the drilling fluids to operate and frequently they indicate different levels merely on change of fluid densities regardless of actual level changes. Pump stroke counters, which measure piston displacement are accurate only to the degree of pump efficiency and most pumps that have been used in the field for any period of time have varying reduced efficiencies. Flow meters are some times affected by foreign particles and have been known to produce inaccurate results. Volumetric accuracies to minimal tolerances are especially desirable in detecting a so called "kick" (incursion of gases and/or formation fluids down-hole) inasmuch as the rate of gas expansion from bottom hole to surface is exponentially increased so that a volume of one barrel at the bottom of the hole might increase to hundreds of barrels at the surface.

Because of the infinite variety of fluid conditions encountered in drilling a well, it is suggested that those devices presently used for measuring drilling mud volumes, all of which have moving parts coming into contact with the fluid itself, have inherent inaccuracies which at times exceed tolerable parameters, and therefore it is desirable to provide a method and a device which can accomplish the measurement of drilling fluid volume and densities without the necessity of having any moving parts coming into contact with the fluid itself. It is also desirable that drilling fluid volumes can be indicated independent of their densities and conversely that densities can be indicated independently of volume. It is desirable that accuracies of less than one barrel pit volume change and 0.075 lb./gallon mud weight change be achieved in order to fall within tolerable parameters; this method and apparatus as hereinafter described accomplishes these goals.

An object of the present invention is to provide a method and apparatus for monitoring mud measuring drilling fluid (mud) weight in each fluid pit of a fluid drilling system.

Another object of the present invention is to provide a method and apparatus for monitoring and measuring drilling fluid (mud) volume in each fluid pit of a fluid drilling system.

A further object of the present invention is to provide a method and apparatus for totalizing drilling fluid (mud) volume in a plurality of fluid pits together with a 24 hour record of said total volume.

A still further object of the present invention is to accomplish the foregoing objects with no moving parts coming into contact with the drilling fluids which have heretofore caused a margin of error by the mud fouling the moving parts of present measuring devices.

A further object of the present invention is to determine mud depth independent of mud weight.

A further object of the present invention is to determine mud weight independent of mud depth.

A further object of the present invention is to provide an early warning indication by furnishing mud weight and change of depth information in the "possum belly."

A still further object of the present invention is to provide a system having the most accurate measurement with sensitivities exceeding prior art devices addressing themselves to the same problem with a minimum of field calibration.

With the foregoing and other objects in view the invention will be more fully described hereinafter and more particularly pointed out in the appended claims.

In the drawings in which like parts are denoted by reference characters throughout the several views.

SUMMARY OF THE INVENTION

This invention provides an accurate method and apparatus for measuring volume and density of fluids in a drilling fluid system. It more specifically provides these measurements at all times during the drilling operations whether going into the hole with the drill pipe or whether removing same or whether in a stand-still condition. It further eliminates the necessity of any moving part required to accomplish any of such measurements from coming into physical contact with the drilling fluids themselves.

The basis for this invention is the general equation for pressure versus depth for any liquid:

where

P = pressure in pounds per square inch
D = depth in feet
$\rho$ = density of liquid in lbs./gallon It will be apparent from the description of the drawings identified as FIGS. 1, 2 and 3, which follow below, that measurement of fluid depth (volumes) can be obtained independently of fluid weights (densities) and conversely that measurement of fluid weights can be obtained independently of fluid depths. (Please note that $P_1$, $P_2$, $D_1$, $D_2$ and $D_3$ are shown on FIG. 1)

Applying the general equation set forth above, the pressure at pickup one ($P_1$) is:

$$P_1 = 0.052 \, D_1 \times \rho$$

The pressure at pickup two ($P_2$) is:

$$P_2 = 0.052 \, D_2 \times \rho$$

Then $$P_2 - P_1 = (0.052 D_2 \times \rho) - 0.052 \, D_1 \times \rho$$

$$1 = 0.052 \, \rho \, (D_2 - D_1)$$

But $$D_2 - D_1 = D_3$$

Then $$P_2 - P_1 = 0.052 \rho D_3$$

or $$\rho = (P_2 - P_1)/0.052 D_3$$

Inasmuch as $D_3$ is a constant fixed distance, the difference between $P_2$ and $P_1$, will be a linear indication of density ($\rho$).

Referring once more to the general equation:

$$P_2 = 0.052 D_2 \rho$$

But $$\rho = (P_2 - P_1)/0.052 D_3$$

Then $$P_2 = 0.052 D_2 (P_2 - P_1)/0.052 D_3$$

$$= (D_2/D_3)(P_2 - P_1)$$

Then $$D_2 = P_2/(P_2 - P_1) D_3$$

But $D_3$ = Constant

Consequently, the depth $D_2$ is a linear function of $(P_2/(P_2 - P_1))$.

Figure 1:
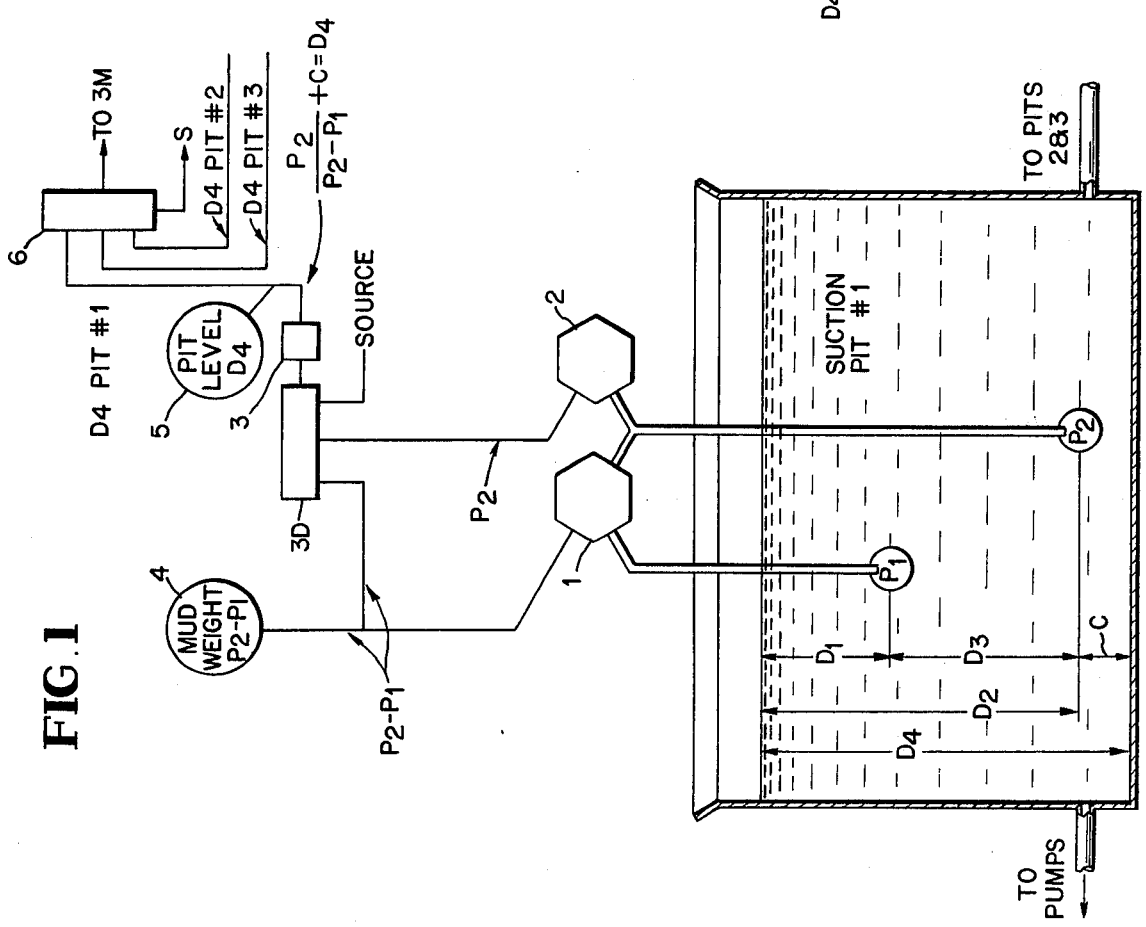
FIG. 1 is a diagrammatic view of the mud weight and depth detector of the present invention applied to a single mud pit.

Referring now to FIG. 1, pressure pick-ups $P_1$ and $P_2$ are connected to a differential pressure transmitter such as a "Taylor Instruments" differential pressure transmitter 1 303 T series A or B manufactured by Taylor Instrument Companies of Rochester, N.Y. the output of which is represented in the above equation as $P_2 - P_1$ and is in fact density or drilling fluid (mud) weight in units of pounds per gallon. $P_2$, is also connected with 2 which is an absolute pressure transmitter. $P_1$ and $P_2$ are pressure pick-ups, bubbler tubes are preferred, however, any suitable pick-up can be used. The output of the absolute pressure transmitter is made available as an input to a Sorteberg Bridge (type D) identified as 3D in the drawing, manufactured by Sorteberg Controls Corp. of Norwalk, Conn. (1973).

The output of the Sorteberg Bridge is transmitted through biasing relay 3 such as a Moore Products Biasing Relay manufactured by Moore Products under U.S. Pat. No. 2,501,957. For the purpose of adding the constant C, that is the mud depth below the probe, $P_2$, with the resultant sum $(P_2/P_2 - P_1) + C$.

As further shown in FIG. 1, the output of 1, the differential pressure transmitter is generated to a gauge 4 which displays mud weights $(P_2 - P_1)$ in units of pounds per gallon. This same output is also led into the Sorteberg dividing bridge 3D in order that $P_2$ may be divided by $P_2 - P_1$ with the resultant quotient added to constant C by the biasing relay, with the biasing relay output representing actual fluid (mud depth) depth $D_4$ which is supplied to 5 a pit level indicating gauge calibrated to show depth of mud in the pit in inches. Thus far, the apparatus and method illustrated in FIG. 1 has furnished mud weight automatically, without the necessity of physically weighing the mud, as is the present method of determining this measurement, while at the same time the depth $D_4$ of the particular pit is made availble to (referring now to FIG. 2) an averaging relay 6, such as a Moore Products relay. The depths ($D_4$ of pits 1, 2 and 3) of all pits are transmitted to the averaging relay 6 the function of which will result in the average depth of all pits fed into it, and this $d_4$ (pits 1, 2 and 3)/3 average depth is fed into a Sorteberg Bridge, multiplying type, 3M where it will be multiplied by a pneumatic pressure representing barrels per foot, brls/ft., which is supplied into the system by pressure regulator 7. This is manually adjusted into the system at the regulator 7. The preferred source of drive in this system is pneumatic, however, the system will function with electrical source as well. The resultant product of the multiplying bridge 3M is total barrels in all pits which is both recorded on a 24 hour recording gauge 8 as well as a continuous gauge 9.

Figure 2:
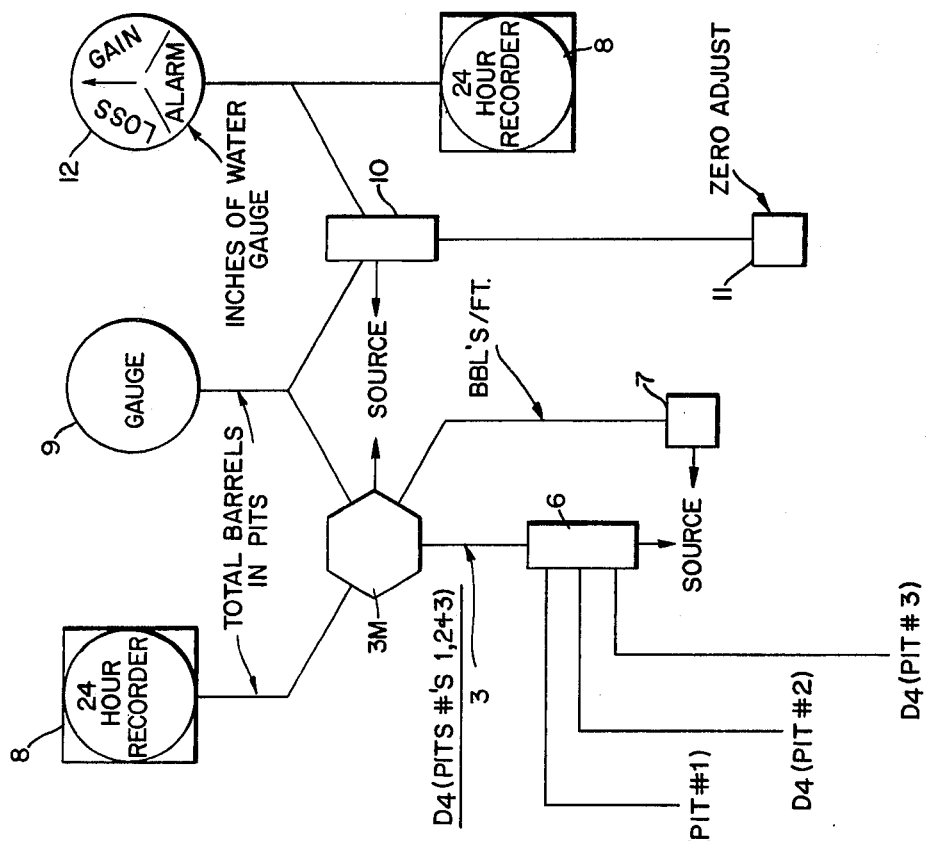
FIG. 2 is a schematic of the inputs from a plurality of mud pits showing total barrels of mud in pits and a gain or loss indicator together with a 24 hour record.

Further referring to FIG. 2, and in particular 10 which is a computing relay, such as a Moore Products Model 68-1, the purpose of this computing relay is to produce a differential in pressure representing change in total barrels of fluids (mud) and this is accomplished when a pressure supply is arbitrarily adjusted through pressure regulator 11 so as to set the index at "zero" on the gain-loss gauge 12. This gain-loss indicator is a 0-15 inches of water gauge with extreme sensitivity in readings and can be calibrated to show gains or losses from 0 to 20 barrels of fluids. A signal alarm can also be set to operate with the desired parameters as chosen by the well operator.

Figure 3:
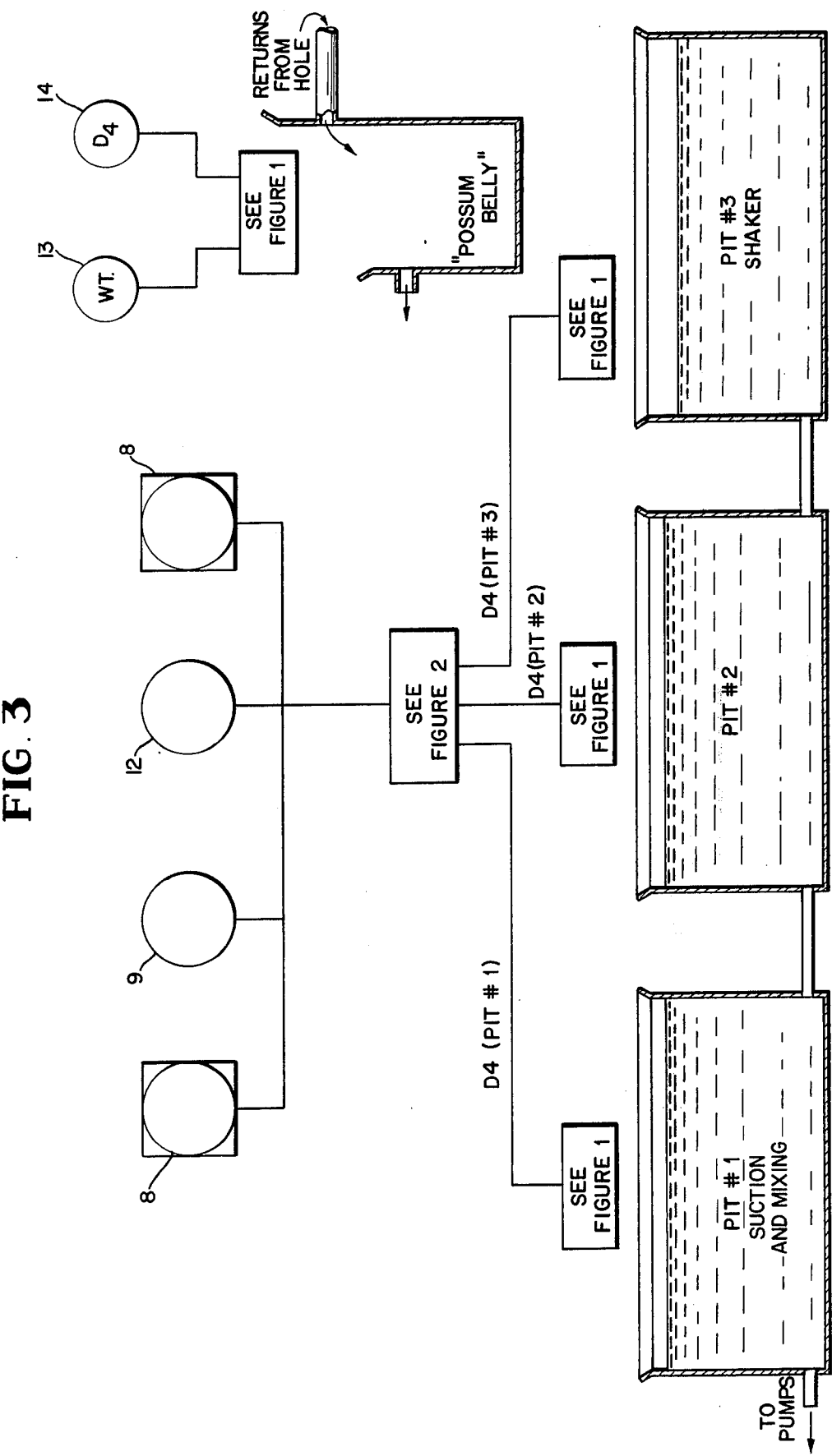
FIG. 3 is a diagrammatic view of the system of FIG. 1 applied to three mud pits and the possum belly.

FIG. 3 illustrates an entire fluid measuring system combining the functions of the system as shown and described in FIGS. 1 and 2. There is however added to this FIG. 3 an additional system entirely devoted to and concerned with furnishing and displaying mud weights and depth 13 and 14 respectively, in the possum belly. These are the depth and weight of drilling fluids as they return from the well bore and many well operators consider this information important as noticeable changes therein may indicate an early warning of a dangerous or unwanted condition down-hole.

What I claim is:

1. The method for measuring volume and density of mud in mud pits in a drilling fluid system comprising the steps of:
   a. placing a first sensor a fixed distance above the bottom of the mud pit,
   b. placing a second sensor a fixed distance above said first sensor in the mud pit,
   c. communicating the output of said first and said second sensors to a differential pressure transmitter,
   d. communicating the output of said first sensor to an absolute pressure transmitter,
   e. introducing the absolute pressure transmitter reading as an input to a Sorteberg bridge,
   f. communicating the output of said differential pressure transmitter to a gauge displaying mud weight in units of pounds per gallon, and as an input to said Sorteberg bridge, and
   g. communicating the Sorteberg bridge output through a biasing relay for adding the constant C mud depth below said first sensor. The output of the biasing relay then represents true depth of fluid level.

2. The method of claim 1 wherein a plurality of mud pits are employed each subjected to the steps of claim 1 further comprising:

a. communicating the biasing relay outputs for all additional pits to an averaging relay to provide an average depth value for all pits fed into it, b. feeding the averaged depth value into a Sorteberg multiplying bridge to be multiplied by a value representing barrels per foot supplied into the system by a pressure regulator the resultant product of said multiplying bridge being total barrels in all pits.

3. The method of claim 2 further comprising:

a. subjecting a pressure supply system to a pressure regulator in said supply system communicating with a computing relay to produce a differential in pressure representing the change in total barrels of fluids when said pressure regulator is indexed at zero, and b. communicating a gain-loss indicator gauge to the output of said computing relay and the output of said Sorteberg multiplying bridge to show gains or losses from 0 to 20 barrels of fluids.

4. The method of claim 1 comprising the step of furnishing and displaying mud weights and volume in the possum belly to provide a reading of the volume and weight of drilling mud as they initially return from the well bore.

5. An apparatus for measuring volume and density of mud in mud pits in a drilling fluid system comprising:

a. a first sensor mounted in a mud pit a fixed distance above the bottom thereof, b. a second sensor located a fixed distance above said first sensor in the mud pit, c. a differential pressure transmitter connected to said first and said second sensor, d. an absolute pressure transmitter connected to said first sensor, e. a Sorteberg bridge connected to receive the absolute pressure transmitter reading as an input, f. the output of said differential pressure transmitter being connected to a gauge displaying mud weight in units of pounds per gallon, and as an input to said Sorteberg bridge, and g. said Sorteberg bridge output being connected to a biasing relay for adding the constant C mud depth below said first sensor, h. said biasing relay output being connected to a pit level indicating gauge showing depth of mud in said pit in inches.

6. The apparatus of claim 5 wherein a plurality of pits are employed each equipped with the apparatus of claim 5 further comprising:

a. an averaging relay connected to said Sorteberg bridge outputs for all additional pits to provide an average depth of all pits fed into it, and b. means feeding the averaged depth into a Sorteberg multiplying bridge to be multiplied by a value representing barrels per foot supplied into the system by a pressure regulator the resultant product of said mutliplying bridge being total barrels in all pits.

7. The apparatus of claim 6 further comprising:

a. a pressure supply system, a pressure regulator in said supply system connected to a computing relay to produce a differential in pressure representing change in total barrels of fluids when said pressure regulator is indexed at zero, and b. a gain-loss indicator gauge connected to the output of said computing relay to show gains or losses from 0 to 20 barrels of fluids.

8. The apparatus of claim 5 further comprising means for furnishing and displaying mud weights and volume in the possum belly to provide a reading of the volume and weight of drilling fluids as they initially return from the well bore.

* * * * *